United States Patent [19]

Rapaport

[11] Patent Number: 5,227,371
[45] Date of Patent: Jul. 13, 1993

[54] UTILIZATION OF ADENINE NUCLEOTIDES AND/OR ADENOSINE AND INORGANIC PHOSPHATE FOR ELEVATION OF LIVER, BLOOD AND BLOOD PLASMA ADENOSINE 5'-TRIPHOSPHATE CONCENTRATIONS

[76] Inventor: Eliezer Rapaport, 142 Payson Rd., Belmont, Mass. 02178

[21] Appl. No.: 400,547

[22] Filed: Aug. 31, 1989

Related U.S. Application Data

[63] Continuation-in-part of Ser. No. 223,503, Jul. 25, 1988, Pat. No. 5,049,372, which is a continuation-in-part of Ser. No. 397,897, Jul. 13, 1982, Pat. No. 4,880,918.

[51] Int. Cl.$^5$ .............................................. A61K 31/70
[52] U.S. Cl. ......................................... 514/46; 514/47
[58] Field of Search ...................... 514/45, 46, 47, 48

[56] References Cited

U.S. PATENT DOCUMENTS

| | | | |
|---|---|---|---|
| 4,141,972 | 2/1979 | Nishino et al. | 424/180 |
| 4,880,918 | 11/1989 | Rapaport | 536/27 |
| 4,923,851 | 5/1990 | Carniglia | 514/48 |
| 5,030,623 | 7/1991 | Gruber | 514/45 |

FOREIGN PATENT DOCUMENTS

| | | |
|---|---|---|
| 0100022 | 2/1984 | European Pat. Off. |
| 52-53897 | 4/1977 | Japan . |
| 55-40635 | 3/1980 | Japan . |
| 56-34697 | 11/1982 | Japan . |

OTHER PUBLICATIONS

"Principles of Biochemistry," Lehninger, The Johns Hopkins University School of Medicine, 1982.
"Biochemistry: The Chemical Reactions of Living Cells," Metzler, 1977.
"Adenosine Metabolism in Human Erythrocytes," Biochimica Et BioPhysica Acta, Meyskens, et al., 1971.
"How Cells Make ATP," Scientific American, Mar. 1978, Hinkle, et al.
Circulation Research, "A Dual Function for Adenosine 5'-Triphosphate in the Regulation of Vascular Tone," vol. 58, No. 3, Mar. 1986, Burnstock, et al.
European Journal of Pharmacology, "Evidence for Two Types of P$_2$-Purinoceptor in Longitudinal Muscle of the Rabbit Portal Vein," 111 (1985) 49-56, Burnstock et al.
Burnstock, "Purinergic Nerves," Pharmacological Reviews, vol. 24, No. 3.
"The Role of Adenosine in the Regulation of Coronary Blood Flow," Circulation Review, Dec. 1980, vol. 47, No. 6, Berne.
"ATP As a Co-Transmitter in Rat Tail Artery," European Journal of Pharmacology, 106 (1985) 149-152, Sneddon, et al.
"Platelet Metabolism and Activation," Seminars in Hematology, vol. 22, No. 3, Jul. 1985, pp. 219-240, Holmsen.
"Adenosine 5'-Triphosphate-(ATP) Mediated Stimulation and Suppression of DNA Synthesis in Lymphoid Cells," The Journal of Immunology, vol. 127, No. 5, Nov. 1981, Ikehara, et al.
"Extracellular ATP Increases Cytosolic Free Calcium in Thymocytes and Initiates the Blastogenesis of the Phorbol 12-Myristate 13-Acetate-Treated Medullary Population," Biochimica et Biophysica Acta, 927 (1987), 437-444, El-Moatassim, et al.

(List continued on next page.)

Primary Examiner—Johnnie R. Brown
Assistant Examiner—J. Oliver Wilson
Attorney, Agent, or Firm—Pollock, Vande Sande & Priddy

[57] ABSTRACT

Administration of adenine nucleotides to a host is followed by their rapid degradation to adenosine and inorganic phosphate which promote increases in liver ATP pools. The turnover of expanded liver ATP pools supply the adenosine precursor for the subsequent expansions of red blood cell (total blood) and blood plasma (extracellular) ATP pools. Thus, the administration of AMP, ATP or their degradation products adenosine and inorganic phosphate to a host, achieve the beneficial increases in liver, total blood and blood plasma ATP levels.

45 Claims, No Drawings

OTHER PUBLICATIONS

"Extracellular ATP Triggers Superoxide Production in Human Neutrophils," Biochemical and Biophysical Research Communications, vol. 162, No. 1, Jul. 14, 1989, Kuroki, et al.

"Experimental Cancer Therapy in Mice by Adenine Nucleotides," Eur. J. Cancer Clin. Oncol., vol. 24, No. 9, pp. 1491–1497, 1988, Rapaport.

"Anticancer Activities of Adenine Nucleotides in Mice are Mediated Through Expansion of Etythrocyte ATP Pools," Proc. Natl. Acad. Sci., vol. 86, pp. 1662–1666, Mar. 1989, Rapaport, et al.

"Extracellular ATP: Effects, Sources and Fate," Biochem. J. (1986) 233, 309–319, Gordon.

"Adenosine and Adenosine Triphosphate for Acute Blood Pressure Control," Seminars in Anesthesia, vol. VII, No. 3, Sep. 1988, 216–225, Flacke.

"State of Adenosine Phosphates During Dehydration of Yeast," Appl. Microbiol. Biotechnol., 1989, 31:194–199, Krallish, et al.

"The Formation of Adenosine in Rabbit Liver and Its Possible Role as a Direct Precursor of Erythrocyte Adenine Nucleotides," The Journal of Biological Chemistry, vol. 249, No. 3, Feb. 10, 1974, pp. 959–966, Lerner, et al.

"Incorporation of Adenosine Into ATP: Formation of Compartmentalized ATP," Proc. Natl. Acad. Sci., vol. 73, No. 9, 3122–3125, Sep. 1976, Rapaport et al.

"Complete Analysis of Cellular Nucleotides by Two-Dimensional Thin Layer Chromatography," The Journal of Biological Chemistry, vol. 257, No. 16, Aug. 1982, 9759–9769, Bochner, et al.

"Adenosine 5'-Triphosphate, Adenosine and Endothelium-Derived Relaxing Factor in Hypoxic Vasodilatation of the Heart," European Journal of Pharmacology, 165 (1989) 323–326, Hopwood, et al.

"Modulation of Platelet Function by Extracellular Adenosine Triphosphate," Blood, vol. 74, No. 3, Aug. 1989, 984–993, Soslau, et al.

"Body Composition Changes in Rats With Experimental Cancer Cachexia: Improvement With Exogenous Insulin," Cancer Research, 48, 2784–2787, May 1988, Moley, et al.

"Cachexia, the Metabolic Component of Neoplastic Diseases," Cancer Research, 37, 2327–2335, Jul. 1977, Costa.

"Cancer Cachexia and Gluconeogenesis," Ann. N.Y. Acad. Sci., 230, 103 (1974), Gold.

"Cachexia, Gluconeogenesis and Progressive Weight Loss in Cancer Patients," J. Theor. Biol., 1978, 73, 51–59, Stein.

"pppA2'p5'A2'p5'A: An Inhibitor of Protein Synthesis Synthesized With An Enzyme Fraction from Interferon-Treated Cells," Proc. Natl. Acad., vol. 75, No. 1, pp. 256–260, Jan. 1978, Kerr et al.

Elmaleh et al., "$^{99m}$Tc-Labelled Nucleotides as Tumor-Seeking Radio Diagnostic Agents," Proc. Natl. Acad. Sci. USA, vol. 81, pp. 918–921 (Feb. 1984).

Chahwala et al., "Extracellular ATP Induces Ion Fluxes and Inhibits Growth of Friend Erythroleukemia Cells," Journal of Biological Chemistry, vol. 259, No. 22 (Nov. 25, 1984), pp. 13717–13722.

*Biochemistry*; Lehninger, Albert L.; pp. 300, 307 and 308; Worth Publishers, Inc., 1970.

Int. J. Tiss. Reac. V. XIII:(4) pp. 219–223 (1991).

UTILIZATION OF ADENINE NUCLEOTIDES AND/OR ADENOSINE AND INORGANIC PHOSPHATE FOR ELEVATION OF LIVER, BLOOD AND BLOOD PLASMA ADENOSINE 5'-TRIPHOSPHATE CONCENTRATIONS

CROSS-REFERENCE TO RELATED APPLICATIONS

This application is a continuation-in-part of co-pending U.S. application Ser. No. 07/223,503 filed Jul. 25, 1988, now U.S. Pat. No. 5,049,372, entitled, "Anticancer Activities in a Host by Increasing Blood and Plasma Adenosine 5'-Triphosphate (ATP) Levels", which in turn is a continuation-in-part of U.S. patent application Ser. No. 06/397,897 filed Jul. 13, 1982, now U.S. Pat. No. 4,880,918, entitled, "Arrest and Killing of Tumor Cells by Adenosine 5'-Diphosphate and Adenosine 5'-Triphosphate", disclosures of which are incorporated herein by reference.

DESCRIPTION

1. Technical Field

The present invention is concerned with the use of adenine nucleotides and/or adenosine and inorganic phosphate separately or in combinations for the purpose of elevating liver, blood (total cellular) and blood plasma (extracellular) levels of adenosine 5'-triphosphate. Because of the extremely rapid degradation of adenine nucleotides; adenosine 5'-monophosphate (AMP), adenosine 5'-diphosphate (ADP) or adenosine 5'-triphosphate (ATP) in the vascular bed by enzymatic activities present in blood plasma and on the membrane of blood cells or vascular endothelium (ectoenzymes), it is widely assumed that the physiological and pharmacological activities of adenine nucleotides after their administration into animals or humans are due to the activity of their degradation product, namely adenosine. The present invention demonstrates that administration of adenine nucleotides (AMP, ADP and/or ATP) or adenosine and inorganic phosphate, which are the degradation products of adenine nucleotides in the peritoneal cavity or in the systemic circulation, into a host, yields elevated levels of liver, blood and blood plasma ATP pools. This finding was totally unexpected and the mechanism accounting for the formation of elevated liver, blood and blood plasma ATP pools has been established and is outlined in the present invention. Since extracellular ATP was shown to produce beneficial effects on a variety of cells and tissues in vitro as ATP and not as one of its degradation products, the present invention offers a variety of beneficial effects in vivo in a host. The reason being that this invention establishes an unexpected process for elevating extracellular (blood plasma) ATP concentrations in such a host. The elevated liver, blood and blood plasma ATP pools are not related to the ATP which is administered to the host since the administered ATP undergoes extremely rapid degradation to adenosine and phosphate. As is demonstrated in this invention, substantial increases in liver, blood and blood plasma ATP pools can also be achieved by the administration of adenine nucleotides other than ATP, or by the administration of their degradation products, namely adenosine and phosphate.

2. Background Art

Extracellular ATP was shown to have a variety of physiological effects on individual cells and tissues. Extracellular ATP was demonstrated to have beneficial physiological effects on the regulation of vascular tone [Burnstock, G. and Kennedy, C. A dual function for adenosine 5'-triphosphate in the regulation of vascular tone. Circul. Res. 58, 319-330 (1986); Kennedy, C. and Burnstock, G. Evidence of two types of $P_2$-purinoceptor in longitudinal muscle of the rabbit portal vein. Eur. J. Pharmacol. 111, 49-56 (1985)], muscle contraction [Burnstock, G. Purinergic nerves. Pharmacol. Rev. 24, 509-581 (1972)], cardiovascular function [Berne, R. M. The role of adenosine in the regulation of coronary blood flow. Circul. Res. 47, 807-813 (1980)], neurotransmission [Sneddon, P. and Burnstock, G. ATP as a cotransmitter in rat tail artery. Eur. J. Pharmacol. 106, 149-152 (1984)], and platelet aggregation [Holmsen, H. Platelet metabolism and activation. Sem. Hematology 22, 219-240 (1985)]. In addition, elevated levels of extracellular ATP were shown to have favorable effects on a variety of blood cells, among then lymphoid cells [Ikehera, S., Pahwa, R. N., Lunzer, D. G., Good, R. A. and Modak, M. J. Adenosine 5'-triphosphate-(ATP) mediated stimulation and suppression of DNA synthesis in lymphoid cells. J. Immunol. 127, 1834-1838 (1981)], thymocytes [El-Moatassin, C., Dornand, J. and Mani, J. C. Extracellular ATP increases cytosolic free calcium in thyocytes and initiates the blastogenesis of the phorbol 12-myristate 13-acetate-treated medullary population. Biochem. Biophys. Acta 927, 437-444 (1987)], and neutrophils (Kuroki, M. and Minakami, S. Extracellular ATP triggers superoxide production in human neutrophils. Biochem. Biophys. Res. Commun. 162, 377-380 (1989)]. Recently, U.S. patent applications by Rapaport (Ser. No. 397, 897,now U.S. Pat. No. 4,880,918 and Ser. No. 223,503, now U.S. Pat. No. 5,049,372) have demonstrated that extracellular levels of ADP and/or ATP inhibit tumor growth and that the administration of adenine nucleotides (AMP, ADP or ATP) into a host result in the elevation of extracellular blood plasma levels of ATP which in turn inhibit tumor growth in a host and also ameliorate cancer cachexia by inhibiting host weight loss in tumor-bearing hosts (See also Rapaport, E. Experimental cancer therapy in mice by adenine nucleotides. Eur. J. Cancer & Clin. Oncol. 24, 1491-1497 (1988); Rapaport, E. and Fontaine, J. Anticancer activities of adenine nucleotides in mice are mediated through expansion of erythrocyte ATP pools. Proc. Natl. Acad. Sci. USA 86, 1662-1666 (1988)).

Because of the extremely rapid breakdown of ATP and other adenine nucleotides to adenosine after their administrations into animals and humans, it has been widely assumed that the beneficial pharmacological effects of ATP or other adenine nucleotides are due to their degradation product, adenosine. In a recent review [Gordon, J. L. Extracellular ATP: effects, sources and fate. Biochem. J. 233, 309-319 (1986)], the author states that "It has been known since 1950 that a bolus of ATP is virtually all removed by a single passage through the lung" and that "there are, apparently, three separate enzymes that sequentially catabolize ATP-→ADP→AMP→Adenosine" (page 316 under subsection Metabolism). In another recent review [Flacke, W. E. Adenosine and adenosine triphosphate for acute blood pressure control. Seminars in Anesthesia 7, 216225 (1988)] the author states that "ATP is rapidly broken down to adenosine after systemic administration, after I.V. administration mainly while transiting the lungs, and the hypotensive effect parallels arterial adenosine concentrations" (page 217).

In light of the many favorable effects exerted by extracellular ATP in vitro on a variety of cells and tissues and the widely accepted knowledge that ATP and other adenine nucleotides are rapidly degraded immediately after their administration into animals or human hosts to their catabolic product adenosine, this invention was completely unexpected and existing art essentially taught away from it. This invention demonstrates that in vivo administered adenine nucleotides or adenosine and inorganic phosphate (but not adenosine alone) or mixtures of these compounds yield a sustained "secondary wave" of extracellular blood plasma ATP levels resulting from the immediate rapid degradation of the administered adenine nucleotides to adenosine and inorganic phosphate which in turn promote the expansion of liver ATP pools followed by expansion of red blood cell (RBC) ATP pools and the release of micromolar levels of ATP from these RBCs into the extracellular (blood plasma) compartment.

Although U.S. patent application Ser. No. 223,503 claims utilization of AMP and ATP for the purpose of elevating total blood (cellular) and blood plasma (extracellular) pools of ATP, the invention outlined in the current application demonstrates that the degradation products of any adenine nucleotide (e.g. AMP, ADP or ATP) namely adenosine and inorganic phosphate (but not adenosine alone) promote the effective elevation of total blood and blood plasma ATP pools in experimental animals which were used to demonstrate this invention in a non-limiting fashion. This process differs from the direct introduction of AMP or ATP by the unexpected mechanistic aspects which are now established and which are outlined in the Summary of the Invention section. Furthermore, this invention is significant for the purpose of elevating liver, blood and plasma ATP pools because the most abundant commercial source of ATP which is yeast, contains mixtures of adenine nucleotides along with adenosine and inorganic phosphate [Krallish, I. L., Damberga B. E. and Beker, M. J. State of adenosine phosphates during dehydration of yeast. Applied Microbiology Biotechnology 31, 194-199 (1989)]. It would be of great commercial advantage not to have to purify these mixtures of adenine nucleotides into their individual components before its utilization for the purpose of expanding liver, blood and plasma ATP pools in a host.

SUMMARY OF THE INVENTION

The present invention demonstrates by the use of mice as experimental hosts in a non-limiting fashion, that the administration of AMP, ADP, ATP, or adenosine and inorganic phosphate (but not adenosine alone) results in the unexpected expansion of liver, red blood cell (RBC) ATP pools and blood plasma ATP levels. These results were demonstrated in experimental animals under normal pathophysiological conditions. In order to demonstrate the invention, high specific radioactivity, radioactively-labeled precursors [$^3$H] or [$^3$H, $\alpha$-$^{32}$P]ATP were administered intraperitoneally into mice in 2 ml of saline or in 2 ml of 35 mM of adenosine, AMP, ATP or adenosine and inorganic phosphate in saline. The results show that adenosine, AMP, ATP or adenosine and inorganic phosphate expand the total liver ATP pools by 2-3 fold as compared to saline or no treatment. However, only AMP, ATP or adenosine and inorganic phosphate yielded expansions of RBC ATP pools and increases in blood plasma ATP levels. Furthermore, the specific radioactivities of liver [$^3$H]ATP pools were similar to the specific radioactivities of RBC [$^3$H]ATP pools after AMP, ATP or adenosine and inorganic phosphate injections, suggesting that the turnover of expanded liver [$^3$H]ATP pools provide the [$^3$H]adenosine precursor which is needed for the enhanced synthesis of RBC ATP pools. Mature RBCs cannot synthesize ATP de novo and require salvage precursors for ATP synthesis [Lerner, M. H. and Lowy, B. A. The formation of adenosine in rabbit liver and its possible role as a direct precursor of erythrocyte adenine nucleotides. J. Biol. Chem. 249, 959-966 (1974)]. Injections of adenosine alone, contrary to injections of adenosine and inorganic phosphate, resulted in expansions of total liver ATP pools without any effects on RBC ATP pools or plasma ATP levels. The specific radioactivity of RBC [$^3$H]ATP pools was vastly different from the specific radioactivity of liver [$^3$H]ATP pools after injections of adenosine or saline containing high specific radioactivity labeled precursors. It is important to note that all the precursors, namely, adenosine, AMP, ATP or high specific radioactivity [$^3$H]ATP are incorporated into liver ATP pools as adenosine or [$^3$H]adenosine respectively. Ectoenzymatic catabolic activities present in the peritoneal cavity and in the vascular bed as well as soluble enzymatic activities present in blood plasma, actively catalyze the degradation of adenine nucleotides to adenosine and inorganic phosphate which was shown to be the combination that promotes the expansion of liver ATP pools followed by the expansions of RBC and blood plasma ATP pools. By the utilization of a doubly labeled [$^3$H,$\alpha$-$^{32}$P]ATP as a high specific radioactivity label, the fate of both the $^3$H-labeled adenosine moiety and the $^{32}$P-labeled inorganic phosphate moiety could be followed. It was shown by this invention that the administered adenine nucleotides are rapidly degraded to adenosine and inorganic phosphate and that the combination of adenosine and inorganic phosphate is required for the expansion of RBC ATP pools. Adenosine alone is sufficient to expand the total liver ATP pools but the inorganic phosphate, which is either a degradation product of adenine nucleotides along with adenosine or is administered along with adenosine, is essential for the expansion of RBC ATP pools. This expansion of RBC ATP pools occurs after the circulating RBCs take-up the adenosine needed for the enhanced salvage synthesis of ATP in RBCs. The circulating RBCs take-up the adenosine, which is produced from the turnover of the expanded liver ATP pools, in the hepatic sinusoids. This fact was demonstrated by the similarity in the specific radioactivities of liver [$^3$H]ATP pools and RBC [$^3$H]ATP pools which lasted for several hours, indicating that these pools effectively mix via a common precursor. When liver [$^3$H]ATP pools were radioactively labeled along with the administration of adenosine or saline, which do not cause expansion of RBC ATP pools, although adenosine treatment does expand the liver ATP pools, the specific radioactivities of liver and RBC [$^3$H]ATP pools were vastly different. The expanded RBC ATP pools are slowly released into the blood plasma (extracellular) compartment in micromolar amounts as was shown by the increases in blood plasma ATP levels, which were determined by bioluminometry and specific radioactivity after expansions of RBC ATP pools achieved by the administration of AMP, ATP or adenosine and inorganic phosphate. The slow continuous release of micromolar amounts of ATP from RBCs containing expanded ATP pools, allows the maintenance of elevated blood plasma ATP pools in spite of the rapid turnover of these pools due to the catabolic activities present in the vascular bed, which effectively degrade these extracellular ATP pools.

BEST AND VARIOUS MODES FOR CARRYING OUT THE INVENTION

The present invention demonstrates in mice as experimental animals utilized in a non-limiting fashion that administration of adenosine 5'-monophosphate (AMP), adenosine 5'-triphosphate (ATP) or mixtures of adenosine and inorganic phosphate (which is any inorganic phosphate salt) result in substantial increases in liver ATP pools, red blood cell (RBC) ATP pools and blood plasma (extracellular compartment) ATP pools. The term pool denotes a steady state concentration which is the result of a specific rate of synthesis and degradation. The significance of this invention is reflected by the facts that many favorable and beneficial (to human hosts) physiological functions are affected by increases in liver, RBCs and blood plasma ATP pools and the commercial availability of mixtures of adenine nucleotides or adenosine and inorganic phosphate rather than pure isolated nucleotides (as reviewed in the Background Art Section). This invention offers therefore new and distinct advantages. The treatment of a host with AMP, ATP, adenosine and inorganic phosphate or mixtures of adenine nucleotides for the purpose of expanding liver, RBC and blood plasma ATP pools can be employed in a pharmaceutically acceptable salt form and can also be employed in a variety of conventional pharmaceutical preparations. These preparations can contain organic or inorganic material suitable for internal administration. The high solubility of AMP and/or ADP and/or ATP salts and/or adenosine and phosphate salts in isotonic aqueous solutions of sodium chloride enable administration of these agents in the form of injection or infusion of single or multiple doses. The injection or infusion can be intraperitoneal, intravenous, or intra-arterial. AMP and/or ADP and/or ATP and/or adenosine and phosphate salts are also suitable for oral, enteral, or topical application when employed with conventional organic or inorganic carrier substances. The effective doses should be in the range of about 1-1,000 mg/kg of body weight per 24 hours for oral or topical administration and 0.01-500 mg/kg of body weight per 24 hours for injections. Intravenous, intraperitoneal, or intraarterial infusions of AMP and/or ADP and/or ATP and/or adenosine and phosphate salts in a suitable salt form is preferably administered at a rate of about 0.001-10 mg/kg of body weight per minute. The delivery of these agents can be performed using a variety of drug delivery systems including, but not limited to, pumps or liposomes.

Examples of inorganic phosphates are sodium phosphate, potassium phosphate and phosphoric acid. The pH of any solution employed containing the phosphate is usually adjusted, if necessary, to about 6.0 to about 7.5 and preferably to about 6.2 to about 7.0 by the addition of a base such as sodium hydroxide. Usually at least about 1 equivalent of phosphate per adenosine is employed.

The following experiments demonstrate the present invention in a non-limiting fashion. Blood (0.25 ml) was collected into 1-ml syringes (26-gauge needles) containing either citrate/dextrose (0.05 ml of 93 mM sodium citrate/7 mm citric acid/140 mM dextrose, pH 6.5) or sodium heparin (0.05 ml of 3 units of sodium heparin in saline) from the inferior vena cava. Mice were anesthetized with ether during the procedure. Plasma or conditioned Hanks' balanced salt solution (HBSS) from the incubation of isolated RBCs was prepared by centrifugation of whole blood or RBCs, respectively, in a Beckman Microfuge (30 sec at $8000 \times g$), and samples of 100 $\mu$l were added to 1 ml of ice-cold 7% (wt/vol) trichloroacetic acid. RBCs were prepared by centrifugation of whole blood ($1500 \times g$ for 5 minutes at 4° C.), and removal of plasma and the buffy coat was followed by a wash of the pelleted RBCs (from 250 $\mu$l of whole blood) in 5 ml of ice-cold HBSS. After centrifugations, the RBC pellet was resuspended in a volume of HBSS to yield the original hematocrit (percent of RBC volume in the whole blood). Aliquots of 20 $\mu$l of RBC suspensions or whole blood were added to 1 ml of ice-cold 7% trichloroacetic acid.

Extraction of acid-soluble nucleotides and determinations of ATP levels by luminometry followed published procedures [Rapaport, E. Experimental cancer therapy in mice by adenine nucleotides. Eur. J. Cancer & Clin. Oncol. 24, 1491-1497 (1988)]. For the determination of total ATP pools and specific radioactivities of [$^3$H]ATP in liver, RBC and blood plasma, blood (0.25 ml) was collected from the inferior vena cava into 1 ml syringes containing 0.05 ml of citrate-dextrose as described previously at a variety of time points after the intraperitoneal injections of AMP, ATP, adenosine and phosphate salts or adenosine alone in saline or injections of saline alone containing in all cases high specific radioactivity [$^3$H]ATP or [$^3$H,$\alpha$-$^{32}$P]ATP as radioactive precursors. Mice were anesthetized with ether during the blood and tissue removing procedure and immediately after the removal of the blood by one person, another person excised a small portion of the liver (250-400 mg) utilizing in situ freeze-clamping with aluminum plates precooled in liquid nitrogen [as described in Rapaport, E. and Zamecnik, P. C. Incorporation of adenosine into ATP:Formation of compartmentalized ATP. Proc. Natl. Acad. Sci. USA 73, 3122-3125 (1976)]. The frozen tissue was pulverized in a mortar at solid carbon dioxide temperatures and extracted in 10 ml of ice-cold 7% trichloracetic acid. Analyses of total liver, RBC and blood plasma ATP pools were performed by bioluminometry as described previously. Conversions of ATP levels to molar concentrations are based on weights of the frozen liver portions or total volume of blood in case of RBCs. The specific radioactivities of liver and RBC [$^3$H,$\alpha$-$^{32}$P]ATP pools and blood plasma [$^3$H]ATP levels were determined by correlation of total radioactivity with total pool size. Total radioactivities of the ATP pools were determined by thin layer chromatography and total pool sizes were determined by bioluminometry. Determination of total radioactivity in blood plasma [$^3$H]ATP required two dimensional thin layer chromatography [according to Bochner, B. R. and Ames, B. N. Complete analysis of cellular nucleotides by two-dimensional thin layer chromatography. J. Biol Chem. 257, 9759-9769 (1982)].

Utilizing radioactively labeled precursors one is able to follow the phosphorylated adenosine derivatives after single i.p. injections of 2 ml of 35 mM adenosine, AMP or ATP. The results reported in Table 1 demonstrate that adenosine, AMP or ATP expand the total liver ATP pools by 2-3 fold as compared to saline treatment. However, only AMP and ATP yielded expansions of RBC ATP pools and increases in blood plasma ATP levels. Furthermore, the specific radioactivities of liver [³H]ATP pools were similar to the specific radioactivities of RBC [³H]ATP pools after AMP or ATP injections, suggesting that the turnover of expanded liver [³H]ATP pools provide the [³H]adenosine precursor which is needed for the expanded synthesis of RBC ATP pools. Mature RBCs cannot synthesize ATP de novo and require salvage precursors for ATP synthesis as discussed earlier. Injections of adenosine resulted in expansions of total liver ATP pools without any effects on RBC ATP pools or plasma ATP levels. The specific radioactivity of RBC [³H]ATP pools was vastly different from the specific radioactivity of liver [³H]ATP pools after injections of adenosine or saline as control (Table 1). It is important to note that all the precursors, namely, adenosine, AMP, ATP or high specific radioactivity [³H]ATP are incorporated into liver ATP pools as adenosine or [³H]adenosine respectively. Ectoenzymatic catabolic activities present in the peritoneal cavity and in the vascular bed as well as enzymatic activities present in blood plasma, actively catalyze the degradation of ATP to adenosine.

The incorporation of a radioactive precursor into liver and RBC [³H]ATP pools after i.p. injections of 2 ml of 35 mM ATP was followed as a function of time (Table 2). The similarity between the specific radioactivities of liver and RBCs [³H]ATP pools was maintained throughout the expansion of the total ATP pools in both the liver (3 to 7 mM) and RBCs (0.6 to 1.7 mM) during the first two hours after injections (Table 2). Only at later times (3–4 hours after injection) did the specific radioactivity of liver [³H]ATP decline at the expense of the increases in the specific radioactivity and size of the RBC [³H]ATP pools (Table 2).

Further studies of the metabolic fate of i.p. injected adenine nucleotides utilizing [³H,α-³²P]ATP as the radioactive precursor show the following (Table 3). Both the phosphate and adenosine moieties of AMP or ATP are incorporated into liver ATP pools and since the phosphate groups of AMP or ATP successfully dilute the ³²P radioactive label, the resulting liver [³H,α-³²P]ATP pools possess progressively lower ³²P/³H ratios in proceeding from adenosine to AMP to ATP as i.p. precursors. The fact that the phosphate groups of AMP and ATP proportionally reduce the ³²P/³H ratios in liver [³H,α-³²P]ATP pools as compared to saline or adenosine injections with [³H,α-³²P]ATP as the radioactive label (Table 3), proves the degradation of [³H,α-³²P]ATP as well as AMP or ATP to adenosine and phosphate moieties prior to incorporation into liver ATP pools. If [³H,α-³²P]ATP as well as AMP or ATP were incorporated en bloc without prior degradation to adenosine and inorganic phosphate, the $^{32}P/^{3}H$ ratios would have remained constant and would not have been proportionally reduced by the phosphate moieties of AMP and ATP. The phosphate groups of AMP or ATP are not necessary for the expansion of total liver ATP pools since adenosine alone was demonstrated to achieve this expansion. Inorganic phosphate however is required for the expansion of RBC ATP pools since 2 ml of 35 mM adenosine along with 105 mM of inorganic phosphate produce results similar to those achieved with 2 ml of 35 mM ATP (Table 3).

The data discussed above lead to the following conclusions:

1. Administrations of adenine nucleotides into a host yield expansions of total liver ATP pools, expansions of RBC ATP pools and blood plasma ATP pools.
2. The administered adenine nucleotides are degraded to adenosine and inorganic phosphate before their promoted expansions of liver, RBC and blood plasma ATP pools.
3. The degradation of adenine nucleotides to adenosine and inorganic phosphate is rapid and occurs in the peritoneal cavity as well as in the vascular bed.
4. A combination of adenosine and inorganic phosphate is needed for the expansions of RBC and blood plasma ATP pools whereas adenosine alone is sufficient for the expansion of liver ATP pool.
5. A mixture of adenosine and inorganic phosphate either administered as such or produced in situ after the administration of adenine nucleotides is necessary and sufficient for achieving the useful expansions of RBC ATP pools and of blood plasma ATP pools.

TABLE 1

Mouse (CB6F₁) liver and RBC [³H]ATP pools and specific radioactivities after i.p. injections of [³H]ATP in saline, adenosine, AMP or ATP*

| Compound Administered | Liver | | RBCs | | Blood Plasma | |
|---|---|---|---|---|---|---|
| | ATP+ mM | ATP cpm/nmol | ATP+ mM | ATP cpm/nmol | ATP+ μM | ATP cpm/nmol |
| Saline | 2.78 | 1543 | 0.69 | 2644 | 0.71 | 3955 |
| Adenosine | 6.86 | 3693 | 0.67 | 2154 | 0.93 | 2637 |
| AMP | 7.63 | 2864 | 1.17 | 2725 | 1.53 | 3293 |
| ATP | 8.29 | 2196 | 1.52 | 2340 | 1.78 | 2819 |

*Mice (CB6F₁, males, 9 weeks old) were injected i.p. with 2 ml of 500 μCi of [³H]ATP (30 Ci/mmol specific radioactivity) in saline, 35 mM adenosine, 35 mM AMP or 35 mM ATP and 2–2.5 hours later the animals were anesthetized and analyzed as described in the text. Data represents the average of two experiments.
+Total ATP pools determined by bioluminometry.
Specific radioactivities were determined by the correlation of cpm in [³H]ATP pools which were determined by one or two dimensional thin layer chromatography with the actual size of the [³H]ATP pool determined by bioluminometry.

TABLE 2

Mouse (CB6F₁) liver and RBC [³H]ATP pools and specific radioactivities after i.p. injections of 2 ml of 35 mM [³H]ATP*

| Time After injection, min | Liver | | RBCs | |
|---|---|---|---|---|
| | ATP+ mM | ATP cpm/nmol | ATP+ mM | ATP cpm/nmol |
| No injection | 3.16 | — | 0.60 | — |
| 15 | 4.24 | 1743 | 0.93 | 1612 |
| 30 | 4.05 | 2408 | 0.99 | 2424 |
| 60 | 7.09 | 2766 | 1.31 | 2671 |
| 120 | 6.13 | 2815 | 1.73 | 3078 |

TABLE 2-continued

Mouse (CB6F$_1$) liver and RBC [$^3$H]ATP pools and specific radioactivities after i.p. injections of 2 ml of 35 mM [$^3$H]ATP*

| Time After injection, min | Liver | | RBCs | |
|---|---|---|---|---|
| | ATP+ mM | ATP cpm/nmol | ATP+ mM | ATP cpm/nmol |
| 240 | 8.25 | 2513 | 2.39 | 3564 |

*Mice (CB6F$_1$ males, 8 weeks old) were utilized. All the experimental procedures are outlined in the text and in the footnotes to Table 1. Data represents the average of two experiments.
+Total pool size.
  Specific radioactivity.

TABLE 3

Mouse (athymic nu/nu) liver and RBC [$^3$H, -$^{32}$P]ATP pools and specific radioactivities after i.p. injections of [$^3$H, α-$^{32}$P]ATP in saline, adenosine, AMP or ATP*

| Compound Administered | Liver | | | RBCs | | |
|---|---|---|---|---|---|---|
| | ATP+ mM | ATP $^3$H-cpm/nmol | ATP $^{32}$P/$^3$H | ATP+ mM | ATP $^3$H-cpm/nmol | ATP $^{32}$P/$^3$H |
| Saline | 2.93 | 1961 | 2.5 | 0.73 | 2874 | 2.5 |
| Adenosine | 6.42 | 2513 | 2.1 | 0.65 | 1063 | 0.4 |
| AMP | 9.10 | 1743 | 1.4 | 1.33 | 1555 | 0.4 |
| ATP | 9.46 | 2376 | 0.6 | 1.64 | 2240 | 0.5 |
| Adenosine + Pi | 7.71 | 1764 | 0.8 | 1.61 | 1899 | 0.6 |

*Mice (athymic nu/nu females, 9 weeks old) were injected i.p. with 2 ml of 500 μCi of [$^3$H]ATP (30 Ci/mmol) and 250 μCi [α-$^{32}$P]ATP (36 Ci/mmol) in saline, 35 mM adenosine, 35 mM AMP, 35 mM ATP or 35 mM adenosine along with 105 mM inorganic phosphate. Animals were analyzed 1½–2 hours after injections as described in the text. The original [$^3$H, α-$^{32}$P]ATP solutions had a $^{32}$P/$^3$H ratio of 1.27. Data represent the average of two experiments. Pi stands for the inorganic phosphate, sodium phosphate.
+Total pool size.
  Specific radioactivity.

Having thus described my invention, what I claim as new and desire to secure by Letters Patent is:

1. A method for increasing total liver ATP pools, total blood ATP pools and blood plasma ATP levels by administering to a mammalian host a member selected from the group consisting of: (a) a mixture of inorganic phosphate and adenosine; and, (b) an adenine nucleotide wherein said adenine nucleotide contains adenosine moiety(ies) and phosphate moiety(ies) and undergo rapid degradation to adenosine and inorganic phosphate after administration to said host.

2. The method of claim 1 wherein a mixture of inorganic phosphate and adenosine is administered to said host and wherein said inorganic phosphate is selected from the group consisting of sodium phosphate, potassium phosphate and phosphoric acid.

3. The method of claim 1 wherein said phosphate employed is an aqueous solution having a pH of about 6.0 to about 7.5.

4. The method of claim 1 wherein said phosphate employed is an aqueous solution having a pH of about 6.2 to about 7.0.

5. The method of claim 1 wherein the amount of combined adenosine and phosphate is about 1–1000 mg/kg of body weight per 24 hours and said administering is oral or topical.

6. The method of claim 1 wherein the amount of combined adenosine and phosphate is about 0.01–500 mg/kg of body weight per 24 hours and said administering is by injection.

7. The method of claim 1 wherein the amount of combined adenosine and phosphate is 0.001–10 mg/kg of body weight per minute and delivery is accomplished by infusion at this rate.

8. The method of claim 1 wherein said host is a human host.

9. The method of claim 1 wherein the source of adenosine and inorganic phosphate are adenine nucleotides that contain adenosine moiety(s) and phosphate moiety(s) and which undergo rapid degradation to adenosine and inorganic phosphate after administration to a host.

10. The method of claim 1 wherein at least about 1 equivalent of phosphate per equivalent of adenosine is employed.

11. The method of claim 1 wherein the molar ratio of adenosine to inorganic phosphate is about 1:1 to about 1:3.

12. A method for increasing the intracellular levels of ATP in a mammalian host by administering to said mammalian host a member selected from the group consisting of: (a) a mixture of inorganic phosphate and adenosine; and, (b) an adenine nucleotides wherein said adenine nucleotides contain adenosine moiety(ies) and phosphate moiety(ies) and undergo rapid degradation to adenosine and inorganic phosphate after administration to said host.

13. The method of claim 12 wherein at least about 1 equivalent of phosphate per equivalent of adenosine is employed.

14. The method of claim 12 wherein total liver ATP pool are increased by administering.

15. The method of claim 12 wherein said host is a human host.

16. The method of claim 12 wherein ATP levels of an organ is increased by said administering.

17. The method of claim 12 wherein the molar ratio of adenosine to inorganic phosphate is about 1:1 to about 1:3.

18. The method of claim 12 wherein adenosine 5'-monophosphate or adenosine 5'-triphosphate is administered to said host.

19. The method of claim 12 wherein an adenine nucleotide is administered to said host and wherein said adenine nucleotide contains adenosine moiety(ies) and phosphate moiety(ies) and undergo rapid degradation to adenosine and inorganic phosphate after administration to a host.

20. The method of claim 12 wherein the amount of combined adenosine and phosphate is about 1–1000 mg/kg of body weight per 24 hours and said administering is oral or topical.

21. The method of claim 12 wherein the amount of combined adenosine and phosphate is about 0.01–500 mg/kg of body weight per 24 hours and said administering is by injection.

22. The method of claim 12 wherein the amount of combined adenosine and phosphate is 0.001–10 mg/kg of body weight per minute and delivery is accomplished by infusion at this rate.

23. A method for increasing cellular level of ATP in an organ but not in red blood cells nor in blood plasma in a mammalian host by administering to said mammalian host adenosine.

24. The method of claim 23 wherein total liver ATP pools are increased by said administering.

25. The method of claim 23 wherein said host is a human host.

26. The method of claim 23 wherein ATP level of an organ is increased by said administering.

27. The method of claim 12 wherein a mixture of inorganic phosphate and adenosine is administered to said host and wherein said inorganic phosphate is selected from the group of sodium phosphate, potassium phosphate and phosphoric acid.

28. The method of claim 12 wherein said phosphate employed is an aqueous solution having a pH of about 6.0 to about 7.5.

29. The method of claim 12 wherein said phosphate employed is an aqueous solution having a pH of about 6.2 to about 7.0.

30. The method of claim 18 wherein adenosine 5'-monophosphate is administered to said host.

31. The method of claim 18 wherein adenosine 5'-triphosphate is administered to said host.

32. A method for increasing extracellular blood plasma levels of ATP in a mammalian host by administering to said host a member selected from the group consisting of: (a) a mixture of adenosine and inorganic phosphate; and, (b) an adenine nucleotides wherein said adenine nucleotides contain adenosine moiety(ies) and phosphate moiety(ies) and undergo rapid degradation to adenosine and inorganic phosphate after administration to said host.

33. The method of claim 32 wherein adenosine 5'-monophosphate is administered to said host.

34. The method of claim 32 wherein adenosine 5'-triphosphate is administered to said host.

35. The method of claim 32 wherein an adenine nucleotide is administered to said host and wherein said adenine nucleotides contain adenosine moiety(ies) and phosphate moiety(ies) and undergo rapid degradation to adenosine and inorganic phosphate after administration to said host.

36. The method of claim 18 wherein the amount of adenosine 5'-monophosphate or adenosine 5'-triphosphate is about 1–1000 mg/kg of body weight per 24 hours and said administering is oral or topical.

37. The method of claim 18 wherein the amount of adenosine 5'-monophosphate or adenosine 5'-triphosphate is about 0.01–500 mg/kg of body weight per 24 hours and said administering is by injection.

38. The method of claim 18 wherein the amount of adenosine 5'-monophosphate or adenosine 5'-triphosphate is 0.001–10 mg/kg of body weight per minute and delivery is accomplished by infusion at this rate.

39. The method of claim 19 wherein the amount of adenine nucleotide is about 1–1000 mg/kg of body weight per 24 hours and said administering is oral or topical.

40. The method of claim 19 wherein the amount of adenine nucleotide is about 0.01–500 mg/kg of body weight per 24 hours and said administering is by injection.

41. The method of claim 19 wherein the amount of adenine nucleotide is 0.001–10 mg/kg of body weight per minute and delivery is accomplished by infusion at this rate.

42. The method of claim 23 wherein the amount of adenosine is about 1–1000 mg/kg of body weight per 24 hours and said administering is oral or topical.

43. The method of claim 23 wherein the amount of adenosine is about 0.01–500 mg/kg of body weight per 24 hours and said administering is by injection.

44. The method of claim 23 wherein the amount of adenosine is 0.001–10 mg/kg of body weight per minute and delivery is accomplished by infusion at this rate.

45. The method of claim 1 wherein said member is in the form of a pharmaceutically acceptable salt.

* * * * *